US00RE50424E

(19) United States
(12) Reissued Patent
Olson

(10) Patent Number: US RE50,424 E
(45) Date of Reissued Patent: *May 13, 2025

(54) NEEDLE COVER ASSEMBLY

(71) Applicant: SHL MEDICAL AG, Zug (CH)

(72) Inventor: Stephan Olson, Stockholm (SE)

(73) Assignee: SHL Medical AG, Zug (CH)

( * ) Notice: This patent is subject to a terminal disclaimer.

(21) Appl. No.: 17/493,095

(22) Filed: Oct. 4, 2021

Related U.S. Patent Documents

Reissue of:
(64) Patent No.: 7,771,397
Issued: Aug. 10, 2010
Appl. No.: 12/471,517
Filed: May 26, 2009

U.S. Applications:
(63) Continuation of application No. 16/930,910, filed on Jul. 16, 2020, now Pat. No. Re. 48,823, which is an application for the reissue of Pat. No. 7,771,397, and a continuation of application No. 16/361,573, filed on Mar. 22, 2019, now Pat. No. Re. 48,172, which is an application for the reissue of Pat. No. 7,771,397, and a continuation of application No. 15/878,699, filed on Jan. 24, 2018, now Pat. No. Re. 47,378, which is an application for the reissue of Pat. No. 7,771,397, and a continuation of application No. 15/481,418, filed on Apr. 6, 2017, now Pat. No. Re. 46,789, which is an application for the reissue of Pat. No. 7,771,397.

(51) Int. Cl.
*A61M 5/32* (2006.01)

(52) U.S. Cl.
CPC ..... *A61M 5/3202* (2013.01); *A61M 5/3204* (2013.01)

(58) Field of Classification Search
None
See application file for complete search history.

(56) References Cited

U.S. PATENT DOCUMENTS 2,860,635 A * 11/1958 Wilburn ..... A61M 5/3202 604/199
5,098,400 A * 3/1992 Crouse et al. ..... 604/192
(Continued)

FOREIGN PATENT DOCUMENTS

EP 1715903 B1 10/2007
FR 2654938 B1 8/1997
(Continued)

*Primary Examiner* — Glenn K Dawson
(74) *Attorney, Agent, or Firm* — McDonnell Boehnen Hulbert & Berghoff LLP

(57) ABSTRACT

A needle cover assembly includes a manually operable member; a rigid needle shield (RNS) provided with an internally arranged resilient cap, in turn arranged to house and protect an injection needle; and a RNS remover assembly including a tubular shaped member surrounding the RNS, in which the tubular shaped member is arranged with at least one grip member capable of gripping the RNS in order to remove the RNS. The RNS remover assembly further includes a spinning attachment member having a distal end fixedly attached to the tubular shaped member and a proximal end rotatably attached to the manually operable member such that the manually operable member can be freely turned in relation to the RNS remover assembly but is locked in an axial direction.

1 Claim, 2 Drawing Sheets

(56) References Cited

U.S. PATENT DOCUMENTS

| | | | | |
|---|---|---|---|---|
| 5,137,516 | A | 8/1992 | Rand et al. | |
| 5,138,537 | A * | 8/1992 | Wang | 362/187 |
| 6,575,939 | B1 | 6/2003 | Brunel | |
| 9,242,050 | B2 | 1/2016 | Abry | |
| RE46,789 | E * | 4/2018 | Olson | A61M 5/3202 |
| RE47,378 | E * | 5/2019 | Olson | A61M 5/3202 |
| 10,307,545 | B2 * | 6/2019 | Maxfield | A61M 5/3204 |
| RE48,172 | E * | 8/2020 | Olson | A61M 5/3202 |
| 10,980,949 | B2 * | 4/2021 | Maxfield | A61M 5/3204 |
| RE48,823 | E * | 11/2021 | Olson | A61M 5/3202 |
| 11,400,234 | B2 * | 8/2022 | Dowds | A61M 5/3204 |
| 11,541,189 | B2 * | 1/2023 | Burren | A61M 5/2033 |
| 2007/0112310 | A1 | 5/2007 | Lavi et al. | |
| 2007/0135767 | A1 | 6/2007 | Gillespie et al. | |
| 2008/0312602 | A1 | 12/2008 | Barrow-Williams et al. | |
| 2009/0054849 | A1 | 2/2009 | Burnell et al. | |
| 2014/0025013 | A1 * | 1/2014 | Dowds | A61M 5/3272 604/198 |
| 2020/0330699 | A1 * | 10/2020 | Burren | A61M 5/2033 |
| 2021/0228814 | A1 * | 7/2021 | Maxfield | A61M 5/3204 |
| 2022/0134018 | A1 * | 5/2022 | Besson | A61M 5/326 604/198 |
| 2023/0021831 | A1 * | 1/2023 | Kalbermatter | A61M 5/2033 |
| 2023/0173186 | A1 * | 6/2023 | Carlsson | A61M 5/3134 604/110 |

FOREIGN PATENT DOCUMENTS

| | | | |
|---|---|---|---|
| GB | 2617389 | | * 10/2023 |
| WO | 98/55168 | A1 | 12/1998 |
| WO | 03/086511 | A1 | 10/2003 |
| WO | 2005/070481 | A1 | 8/2005 |
| WO | WO 2005115508 | A1 | * 12/2005 |
| WO | 2006/106290 | A1 | 10/2006 |
| WO | 2007/047200 | A1 | 4/2007 |
| WO | 2008/094984 | A2 | 8/2008 |
| WO | 2009/019440 | A1 | 2/2009 |
| WO | 2009/040601 | A1 | 4/2009 |
| WO | 2009/040603 | A1 | 4/2009 |
| WO | 2009/081103 | A1 | 7/2009 |
| WO | 2009/114542 | A1 | 9/2009 |
| WO | 2010/007395 | A1 | 1/2010 |

* cited by examiner

NEEDLE COVER ASSEMBLY

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

*CROSS-REFERENCE TO RELATED APPLICATIONS*

*This application is a continuation reissue application of reissue application Ser. No. 16/930,910, filed Jul. 16, 2020, which is a continuation reissue application of reissue application Ser. No. 16/361,573, filed Mar. 22, 2019, now U.S. Reissue Pat. No. RE 48,172 E, which is a continuation reissue application of reissue application Ser. No. 15/878,699, filed Jan. 24, 2018, now U.S. Reissue Pat. No. 47,378 E, which is an application for the reissue of U.S. Pat. No. 7,771,397, and a continuation reissue application of reissue application Ser. No. 15/481,418, filed Apr. 6, 2017, now U.S. Reissue Pat. No. RE 46,789 E, which is an application for reissue of U.S. Pat. No. 7,771,397, which issued on Aug. 10, 2010.*

*Notice: More than one reissue application has been filed for the reissue of U.S. Pat. No. 7,771,397. The reissue applications are the present continuation reissue application, U.S. Reissue patent application Ser. No. 16/930,910, filed Jul. 16, 2020, U.S. Reissue patent application Ser. No. 16/361,573, filed on Mar. 22, 2019, now U.S. Reissue Pat. No. RE 48,172 E, which is a continuation reissue application of U.S. Reissue patent application Ser. No. 15/878,699, filed on Jan. 24, 2018, now U.S. Reissue Pat. No. 47,378 E, which is a continuation reissue application of U.S. Reissue patent application Ser. No. 15/481,418, filed on Apr. 6, 2017, now U.S. Reissue Pat. No. RE 46,789 E.*

TECHNICAL AREA

The present invention relates to a needle cover assembly and in particular to a needle cover assembly for preventing breakage of the needle during removal of the cover.

BACKGROUND

There are many medicament delivery devices on the market that have been developed for self administration of medicament, where one large group is medicament injection devices. Many of these injection devices have been provided with removable needle cover assemblies where the core cover is a so called Rigid Needle Cover or Rigid Needle Shield (RNS).

These RNSs are arranged to protect the injection needle before use in order to keep the needle sterile and also protect from unintentional needle sticks. Many of these RNSs are pushed onto the neck portion of a medicament container, such as a syringe, where the RNS are provided with an inner cap in contact with the surface of the syringe. The inner cap is preferably of a resilient material, normally rubber that ensures a tight grip and a good seal between the cap and the syringe. However this tight grip entails a problem in that it is difficult to remove the RNS from the syringe in order to perform an injection.

Therefore a number of RNS removal devices have been developed, which are intended to aid the user in removing the RNS. International Publications WO2007/047200, WO 2006/106290, and WO 2005/115508 disclose different solutions to this problem. However, they all include a function where the whole assembly, including the RNS and its resilient inner cap, are twisted or rotated. This a major drawback since this twisting action of the inner cap very easily causes damage to the injection needles, which usually are thin and easily bendable such that when the RNS is removed, the needle has become so damaged it cannot be used for the injection.

International Publication WO 2009/01440 discloses an injection device comprising a cap including a central boss. A needle shield retainer provided with a shield grip and a shield pull component connected to the shield grip fits inside the central boss and can grip a needle shield tightly. Thus, as the cap is pulled off the housing, the needle shield is pulled away from the syringe with the cap. In addition, a first screw thread is provided on outside of the shield pull component which engages with a second screw thread provided on the inside of central boss.

Before injection, a user first rotates the cap many turns about the longitudinal axis away from the exit aperture. During rotation, the needle shield retainer does not rotate relative to a discharge nozzle and the rotational movement of the cap relative to the housing is converted into linear movement of the needle shield retainer away from the exit aperture in the axial direction achieved through engagement of the screw threads so the needle shield is pulled away from the discharge nozzle through the exit aperture into the central boss. After rotation, the user finally pulls the cap away from the housing, the needle shield and the discharge nozzle are not engaged with each other, and the cap becomes completely detached from the injection device.

The device according to WO 2009/01440 does not thus twist or rotate the needle shield but a rotational interaction with threaded components causes a linear movement of the needle shield retainer from the exit aperture of the medicament delivery device. The solution according to WO 2009/01440 does however include a number of components in order to obtain the aided linear movement of the needle cover assembly in order to remove the needle shield and is thus rather costly to manufacture. However, patients suffering from reduced hand dexterity experience difficulties in grasping and releasing the cap when it has to be rotated many turns.

There is thus a need for needle shield removal devices that provide the desired function without the risk of damaging injection needles and that at the same time are not so complex regarding use and manufacture.

SUMMARY

An aim of the present invention is to provide a needle cover assembly that remedies the risks of the above mentioned devices regarding damaging injection needles when removing the needle cover assemblies.

According to an aspect of the invention, a needle cover assembly includes a manually operable member; a rigid needle shield RNS provided with an internally arranged resilient cap, in turn arranged to house and protect an injection needle; and a RNS remover assembly including a tubular shaped member surrounding the RNS, in which the tubular shaped member is arranged with at least one grip member capable of gripping the RNS in order to remove the RNS. The RNS remover assembly further includes a spinning attachment member having a distal end fixedly attached to the tubular shaped member and a proximal end rotatably attached to the manually operable member such that the manually operable member can be freely turned in relation to the RNS remover assembly but is locked to the RNS remover assembly in an axial direction.

According to another aspect of the invention, an annular distal end surface of the manually operable member is arranged to be in contact with a corresponding proximally directed annular surface of a housing of a medicament delivery device to which the needle cover assembly can be releasably attached. The surfaces form an interface having a wave or cam shape such that when the manually operable member is turned in relation to the housing, the RNS remover assembly is moved in an axial proximal direction without rotation.

Other aspects of the invention are that the at least one grip member includes pointed tabs directed inclined in the proximal direction, capable of being pushed through openings on the RNS and into the material of the resilient cap; that the tubular shaped member of the RNS remover assembly is made of a metallic material; that the manually operable member is provided with manual grip areas on its outer circumference surface to enhance the manual gripping of the cap cover; and that the manual grip areas include different geometrical shapes for providing tactile information.

There are a number of advantages with the present invention. For example, due to the rotational movement of the manually operable member in relation to the RNS remover assembly, the manually operable member can be turned without the risk of damaging the injection needle which is the case with the known solutions where the whole needle cover assembly is turned.

The turning also enables an initial axial movement of the manually operable member in relation to the housing and thus the injection needle attached to a medicament container due to the wave or cam interface between the cap cover and the housing providing an important aid in the initial axial movement of the cap cover, the RNS remover assembly and thus the RNS. This initial aid can be important because it has been found that it may require up to 4 kilograms (kg) of load in order to release the RNS from the injection needle and the neck of the medicament container. If only an axial pulling force would be applied to the cap cover, it would be very difficult for some users to remove the needle cover assembly. There would also be a pronounced risk of damaging (e.g., bending) the injection needle during the process.

The tubular shaped member of the RNS remover assembly is preferably arranged with grip devices that are forced into the resilient cap material of the RNS, providing a very tight and secure gripping action, ensuring that the RNS is readily removed when the manually operable member is pulled from the device. Further in order to ascertain the secure gripping action, metallic materials are preferred and not plastic, since the metallic materials provide a much thinner tubular member of the RNS remover assembly, thereby making the needle cover assembly smaller in diameter.

These and other aspects and advantages of the present invention will become apparent from the following detailed description and from the accompanying drawings.

BRIEF DESCRIPTION OF THE DRAWINGS

In the following detailed description of the invention, reference will be made to the accompanying drawings, of which

DETAILED DESCRIPTION

In the present application, the term "distal part/end" refers to the part/end of the medicament delivery device, or the parts/ends of the members thereof, which under use of the medicament delivery device is located the farthest away from the medicament delivery site of the patient. Correspondingly, the term "proximal part/end" refers to the part/end of the medicament delivery device, or the parts/ends of the members thereof, which under use of the device is located closest to the medicament delivery site of the patient.

Figure 1:
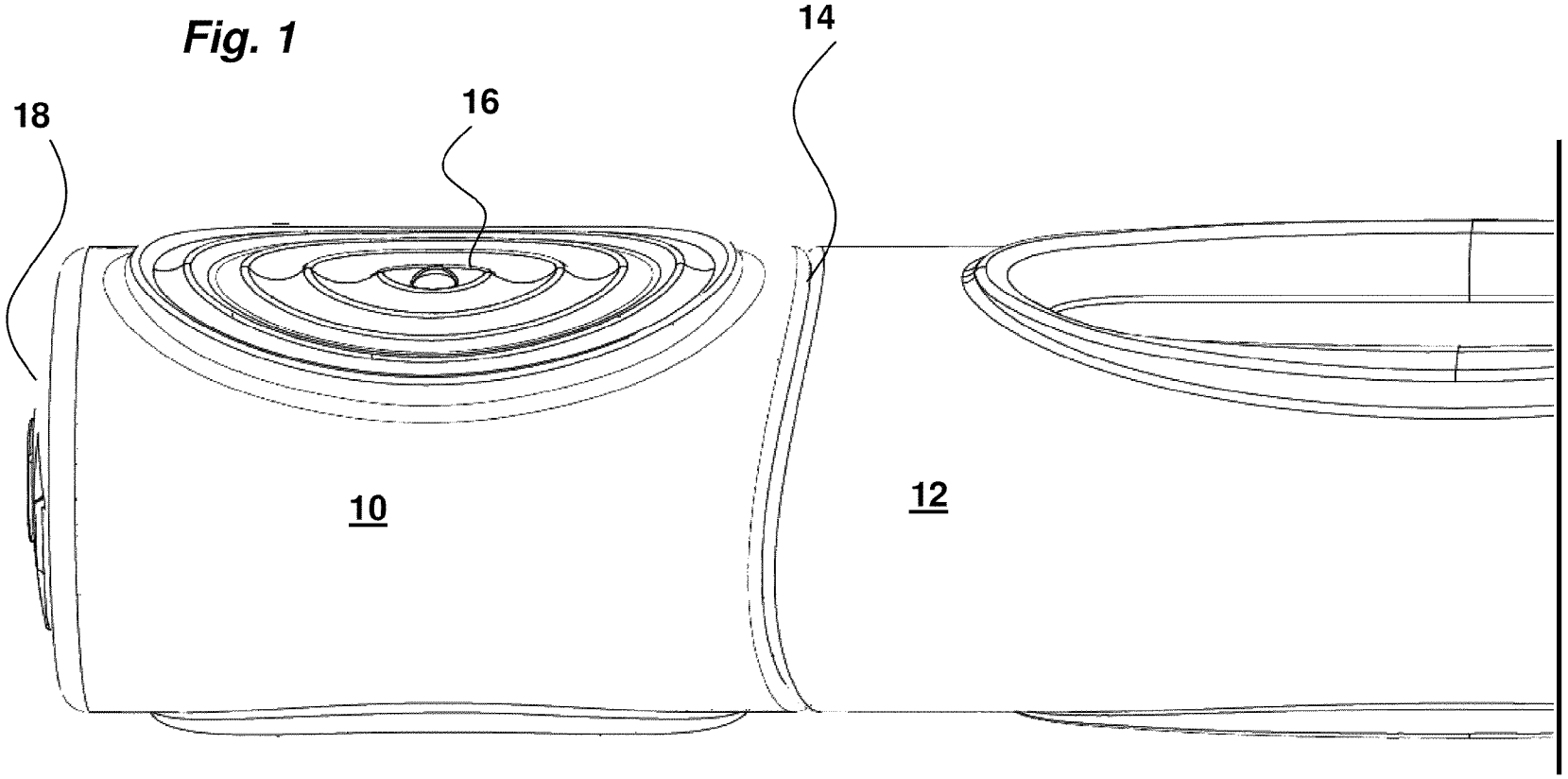
FIG. 1 is a side view of a proximal part of a medicament delivery device comprising the present invention.
Figure 2:
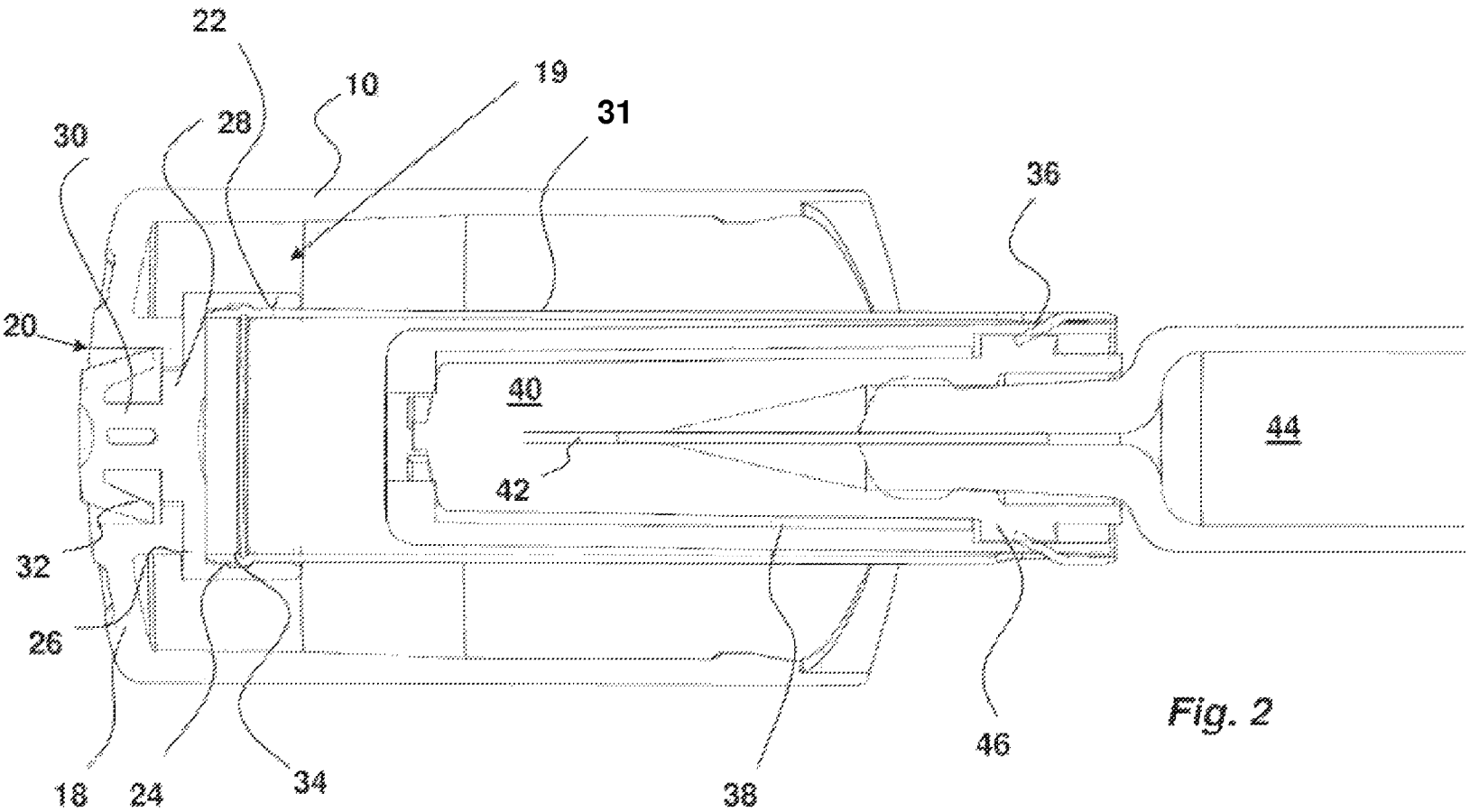
FIG. 2 is a side view of one embodiment of the present invention in a cross-section.

FIGS. 1 and 2 show one embodiment of the present invention. A needle cover assembly includes a generally tubular manually operable member 10; a rigid needle shield (RNS) 38 provided with an internally arranged resilient cap 40, in turn arranged to house and protect an injection needle 42; and a RNS remover assembly, including a tubular shaped member 31 surrounding the RNS 38. The tubular shaped member 31 is arranged with at least one grip member 36 capable of gripping the RNS in order to remove the RNS. The RNS remover assembly further includes a spinning attachment member 19 having a distal end fixedly attached to the tubular shaped member 31 and a proximal end rotatably attached to the manually operable member 10 such that the manually operable member can be freely turned in relation to the RNS remover assembly but is locked in an axial direction.

The manually operable member 10 is designed to fit over the proximal end of a medicament delivery device, forming a unit with the housing 12 of the medicament delivery member. As seen in FIG. 1, the annular contacting end surfaces of the manually operable member 10 and the housing 12 form an interface 14 having wave or cam shapes, as will be described below.

The manually operable member 10 is further provided with at least one grip area 16 having protrusions and valleys to provide a proper grip of the manually operable member. These protrusions and valleys may be formed of different geometries to provide tactile information regarding, for example, the type of drug, strength, and the like, that facilitates for a user with impaired vision to retrieve information from the device.

The manually operable member 10 is provided with a proximal end wall 18 provided with a central opening 20. The spinning attachment member 19 is positioned inside the manually operable member adjacent the end wall 18. The spinning attachment member 19 includes a tubular shaped section 22 arranged with a circumferential groove 24 on its inner surface. The tubular section 22 is arranged with an end wall 26 having a circularly shaped ledge 28 extending towards the proximal direction though the central opening 20. The circular ledge 28 is arranged with a centrally positioned stem 30 protruding in the proximal direction through the opening 20. The proximal end of the stem 30 is provided with flexible arms 32 directed inclined in the distal direction such that they prevent axial movement between the manually operable member 10 and the spinning attachment member 19 but allow rotational movement between them.

The proximal end of the tubular shaped member 31 is arranged with an outwardly directed circumferential ledge 34 arranged to fit into the annular groove 24 of the spinning attachment member 19. At the distal end of the tubular shaped member 31, pointed tabs 36 are arranged directed towards the proximal end at an inwardly inclined direction.

The resilient cap 40 made of a rubber material is designed to house and protect an injection needle 42 and intended to be attached to or made integral with a medicament container 44. Moreover, the RNS 38 is arranged with openings 46 through which the pointed tabs extend.

The needle cover assembly is intended to function as follows. When the injection needle is to be used for an injection of a dose of medicament, the needle cover assembly has to be removed. The user then grips the grip areas 16 with his/her fingers. In order to start the removal of the needle cover assembly, the user twists the manually operable member 10 in the circumferential direction. This causes the annular surfaces of the interface 14 between the manually operable member and the housing to slide relative each other, and due to the wave or cam shapes, the manually operable member 10 is also moved axially in relation to the housing 12.

However it is only the manually operable member 10 of the needle cover assembly that is turned; the other parts are stationary due to the connection between the manually operable member 10 and the spinning attachment member 19. When the wave or cam shapes have reached their "highest" positions, the manually operable member 10 can no longer be moved axially by twisting. However, now the initially high forces required to hold the RNS and its resilient cap attached to the container have been overcome. The user now quite easily pulls the needle cover assembly in the axial proximal direction. This causes the tubular shaped member 31 also to move axially, whereby the pointed tabs 36 are forced through the openings 46 of the RNS into the rubber material of the resilient cap 40, whereby also the RNS 38 and its resilient cap 40 are moved in the axial proximal direction and thus the needle cover assembly is removed and the injection needle 42 is exposed.

It is thus to be understood that the embodiments described above and shown in the drawings are to be regarded only as non-limiting examples of the present invention and that it may be modified within the scope of the patent claims. Thus there are many other mechanical solutions as how the manually operable member is capable of rotating in relation to the RNS remover assembly. The disclosed stem with its inclined flexible arms are an example of how manually operable member and the RNS remover assembly may be assembled in that the stem is pushed through the opening whereby the arms flex radially inwards, enabling them to pass through the opening. When the flexible arms have then passed the opening they flex outward and lock the manually operable member to the RNS remover assembly in the axial direction. However other such solutions readily available to the person skilled in the art may be employed.

It is to be understood that the embodiment described above and shown in the drawings is to be regarded only as a non-limiting example of the present invention and that it may be amended in many ways within the scope of the patent claims.

What is claimed is:

[1. A needle cover assembly, comprising:

a manually operable member having an annular distal end surface; a housing of a medicament delivery device having a corresponding proximally directed annular surface in contact with the distal end surface, the housing can be releasably attached to the manually operable member; wherein the surfaces form an interface having a wave or cam shape;

a rigid needle shield (RNS) having an internally arranged resilient cap, in turn arranged to house and protect an injection needle; and a RNS remover assembly, comprising:

a tubular shaped member surrounding the RNS, wherein the tubular shaped member is arranged with at least one grip member capable of gripping the RNS in order to remove the RNS, and a spinning attachment member having a distal end fixedly attached to the tubular shaped member and a proximal end rotatably attached to the manually operable member such that when the manually operable member is turned in relation to the housing, the RNS remover assembly is moved in an axial direction without rotation.]

[2. The needle cover assembly of claim 1, wherein the at least one grip member comprises pointed tabs inclined in the proximal direction and configured to be pushed through openings on the RNS and into the resilient cap.]

[3. The needle cover assembly of claim 2, wherein the tubular shaped member is made of a metallic material.]

[4. The needle cover assembly of claim 2, wherein the manually operable member has manual grip areas on its outer circumference surface to enhance manual gripping of a cap cover.]

[5. The needle cover assembly of claim 4, wherein the manual grip areas have different geometrical shapes for providing tactile information.]

[6. The needle cover assembly of claim 1, wherein the tubular shaped member is made of a metallic material.]

[7. The needle cover assembly of claim 6, wherein the manually operable member has manual grip areas on its outer circumference surface to enhance manual gripping of a cap cover.]

[8. The needle cover assembly of claim 7, wherein the manual grip areas have different geometrical shapes for providing tactile information.]

[9. The needle cover assembly of claim 1, wherein the manually operable member has manual grip areas on its outer circumference surface to enhance manual gripping of a cap cover.]

[10. The needle cover assembly of claim 9, wherein the manual grip areas have different geometrical shapes for providing tactile information.]

*11. A medicament delivery device comprising:*

*an outer housing having a proximal end that has an annular end surface;*

*a container filled with medicament positioned within the housing, where the container has a neck having an outer surface;*

*a needle having a distal end and a proximal end, where the distal end is fixedly attached to the neck and in fluid communication with the medicament;*

*a resilient cap comprising a rubber material that covers and protects the proximal end of the needle and is engaged with the outer surface of the neck;*

*a rigid needle shield (RNS) covering the resilient cap, wherein the resilient cap is internally arranged in the RNS; and where the RNS comprises a tubular wall having one or more through openings;*

*a manually operable member comprising a manual grip area located on an outer surface of the manually operable member, wherein the housing can be releasably attached to the manually operable member, where the manually operable member has an annular distal end surface that engages with the annular end surface of the housing to form an interface having a wave or cam shape, where the manual grip area comprises*

*different geometrical shapes that protrude radially outward from the outer surface of the manually operable member; and*

*a RNS remover assembly, comprising:*

*a tubular shaped member surrounding the RNS, where the tubular shaped member comprises grip members having internal and radially directed surfaces that are inclined in a proximal direction such that upon axial proximal movement of the tubular shaped member relative to the neck of the container the internal and radially directed surfaces capable of gripping the RNS such that the RNS and resilient cap moves proximally with the tubular shaped member, wherein a proximal end of the tubular shaped member is axially fixed to a distal end of a spinning attachment member, wherein a proximal end of the spinning attachment member is rotatably attached to the manually operable member, and wherein the distal end of the spinning attachment member is axially fixed to the manually operable member such that the manually operable member freely turns relative to tubular shaped member,*

*wherein rotation of the manually operable member relative to the housing causes the RNS, the RNS remover assembly, and the resilient cap to each move in an axial direction, without rotation, in the proximal direction such that the resilient cap is disengaged from the neck of the container, and*

*wherein rotation of the manually operable member causes the annular distal end surface of the manually operable member to disengage from the annular end surface of the housing such that the manually operable member, the RNS, the RNS remover assembly, and the resilient cap can be separated from the housing to expose the proximal end of needle.*

* * * * *